(12) United States Patent
Sun

(10) Patent No.: US 11,224,607 B2
(45) Date of Patent: Jan. 18, 2022

(54) ANTICANCER COMPOSITION OF TRADITIONAL CHINESE MEDICINE AND PREPARATION METHOD THEREOF

(71) Applicant: Deyu Sun, Apple Valley, CA (US)

(72) Inventor: Deyu Sun, Apple Valley, CA (US)

( * ) Notice: Subject to any disclaimer, the term of this patent is extended or adjusted under 35 U.S.C. 154(b) by 22 days.

(21) Appl. No.: 16/713,450

(22) Filed: Dec. 13, 2019

(65) Prior Publication Data

US 2021/0177873 A1 Jun. 17, 2021

(51) Int. Cl.

| | |
|---|---|
| *A61K 36/00* | (2006.01) |
| *A61K 31/704* | (2006.01) |
| *A61K 36/481* | (2006.01) |
| *A61K 36/9066* | (2006.01) |
| *A61K 36/902* | (2006.01) |
| *A61K 36/638* | (2006.01) |
| *A61K 9/16* | (2006.01) |
| *A61K 36/539* | (2006.01) |
| *A61K 36/28* | (2006.01) |
| *A61K 31/05* | (2006.01) |
| *A61K 9/00* | (2006.01) |
| *A61K 9/48* | (2006.01) |
| *A61K 36/484* | (2006.01) |

(52) U.S. Cl.
CPC .......... *A61K 31/704* (2013.01); *A61K 9/0053* (2013.01); *A61K 9/167* (2013.01); *A61K 9/4891* (2013.01); *A61K 31/05* (2013.01); *A61K 36/28* (2013.01); *A61K 36/481* (2013.01); *A61K 36/484* (2013.01); *A61K 36/539* (2013.01); *A61K 36/638* (2013.01); *A61K 36/902* (2013.01); *A61K 36/9066* (2013.01)

(58) Field of Classification Search
CPC ........................... A61K 9/4891; A61K 9/5005
See application file for complete search history.

*Primary Examiner* — Qiuwen Mi
(74) *Attorney, Agent, or Firm* — Novoclaims Patent Services LLC; Mei Lin Wong

(57) ABSTRACT

A medication of natural Chinese medicine with sustained release for cancer treatment and its preparation method thereof contains active ingredients of: ginsenoside, *Astragalus* polysaccharide, zedoary (*Curcuma zedoaria*), river bulrush (*Sparganium stolonferum Buch.-Ham*), Ternstroemia gymnanthera, Fructus Ligustri Lucidi, licorice, Chinese skullcap (*Scutellaria baicalnsis Georgi*), Sculellaria barbata, paclitaxel, *Silybum marianum* (L.) Gaertn., and Cannabidiol (CBD). The drug can restore body balance and promote self-recovery. The drug can be used as an alternative medicine or can be used in combination with conventional cancer treatment, and is especially target for patients suffered from toxic side effects of radiotherapy and chemotherapy, which can increase the efficiency and reduce the toxicity of conventional cancer treatment and eliminate side effects of vomiting, hair loss, and unbearable soreness of the body.

5 Claims, 1 Drawing Sheet

| Name in English | Name used in Traditional Chinese Medicine | Weight / gram | Percentage weight |
|---|---|---|---|
| Ginsenoside | 人参皂苷 | 5-10 | 2.19-6.30% |
| Astragalus polysaccharide | 黄芪多糖 | 7-15 | 3.07-9.22% |
| Zedoary (*Curcuma zedoaria*) | 莪术 | 10-20 | 4.39-12.10% |
| River bulrush (*Sparganium stoloniferum Buch.-Ham*) | 三棱 | 10-15 | 4.39-9.45% |
| Extract of *Ternstroemia gymnanthera* | 厚皮香提取物 | 10-15 | 4.39-9.45% |
| *Fructus Ligustri Lucidi* | 女贞子 | 12-20 | 5.26-12.30% |
| *Licorice* | 甘草 | 5-9 | 2.18-5.72% |
| *Chinese skullcap* (*Scutellaria baicalnsis Georgi*) extract | 黄芩提取物 | 12-19 | 5.26-11.78% |
| *Sculellaria barbata* | 半枝莲 | 15-20 | 6.58-12.61% |
| Paclitaxel | 紫杉醇 | 13 | 5.54-8.55% |
| *Silybum marianum (L.) Gaertn.* micropoweder | 水飞大小蓟微粉 | 15-20 | 6.58-12.61% |
| Cannabidiol | CBD | 38-176 | 25%-50% |

Table 1: Active ingredients of Medication of Traditional Chinese Medicine for Cancer Treatment

ANTICANCER COMPOSITION OF TRADITIONAL CHINESE MEDICINE AND PREPARATION METHOD THEREOF

BACKGROUND OF THE PRESENT INVENTION

Field of Invention

The present invention relates to the field of traditional Chinese medicine, and more particularly to an oral form medication of natural Chinese medicine with sustained release for cancer treatment and its preparation method thereof.

Description of Related Arts

Common cancer treatment includes surgery, radiotherapy, chemotherapy and target drug therapy. It is common for cancer patients to have soreness or pain. Cancer patients may also feel very tired and lack of physical strength. The cancer treatment is usually target at removing or killing the cancer cells by external means. There is not much consideration about the restoration of our body balance or the self-recovery mechanism of our body. There is also lack of oral form composition of natural Chinese medicine with sustained release which is natural, non-toxic, non-invasive but effective to cancer treatment.

SUMMARY OF THE PRESENT INVENTION

An object of the present invention is to provide a medication of natural Chinese medicine with sustained release in oral form for cancer treatment and its preparation method thereof.

Another object of the present invention is to provide a medication of natural Chinese medicine with sustained release in oral form for cancer treatment which is targeted at providing relieve to a cancer's patient and prolonging the patient's life.

According to a preferred embodiment of the present invention, a medication of traditional Chinese medicine with sustained release for cancer treatment contains active ingredients of: 5-10 grams of ginsenoside, 7-15 grams of *Astragalus* polysaccharide, 10-20 grams of zedoary (*Curcuma zedoaria*), 10-15 grams of river bulrush (*Sparganium stolonferum Buch.-Ham*), 10-15 grams of extract of *Ternstroemia gymnanthera*, 12-20 grams of *Fructus Ligustri Lucidi*, 5-9 grams of *licorice*, 12-19 grams of Chinese skullcap extract (*Scutellaria baicalnsis Georgi*), 15-20 grams of *Sculellaria barbata*, 13 grams of paclitaxel, 15-20 grams of micropowder of *Silybum marianum* (L.) *Gaertn.*, and 25-50% of Cannabidiol powder by percentage weight of total active ingredients.

The weight of Cannabidiol powder is about 38-176 grams.

According to another preferred embodiment of the present invention, a medication of traditional Chinese medicine with sustained release for cancer treatment contains active ingredients by percentage weight of: 2.19-6.30% ginsenoside, 3.07-9.22% *Astragalus* polysaccharide, 4.39-12.10% zedoary (*Curcuma zedoaria*), 4.39-9.45% river bulrush (*Sparganium stoloniferum Buch.-Ham*), 4.39-9.45% extract of *Ternstroemia gymnanthera*, 5.26-12.30% *Fructus Ligustri Lucidi*, 2.18-5.72% *licorice*, 5.26-11.78% extract of Chinese skullcap (*Scutellaria baicalnsis Georgi*), 6.58-12.61% *Sculellaria barbata*, 15.54-8.55% paclitaxel, 6.58-12.61% micropowder of *Silybum marianum* (L.) *Gaertn.*, and 25-50% Cannabidiol powder.

The medication of traditional Chinese medicine with sustained release for cancer treatment is prepared into an oral form, which includes coated pellet form, capsule form and liquid form.

According to another preferred embodiment of the present invention, the medication in pellet form is prepared by the steps of: (a) Carrying out extraction for zedoary (*Curcuma zedoaria*), river bulrush, *Fructus Ligustri Lucidi*, licorice, and *Sculellaria barbata*, to obtain a first composition; (b) Mixing ginsenoside, *Astragalus* polysaccharide, *Ternstroemia gymnanthera* extract, Chinese skullcap extract, *Silybum marianum* (L.) *Gaertn.* micropowder, paclitaxel, CBD powder and starch by a mixer to obtain a second composition; (c) Placing the first composition, the second composition, and microcrystalline cellulose in a fluidized bed, and spraying distilled water so that the first composition, the second composition, and the microcrystalline cellulose are bonded to form pellets; (d) Allowing the pellets to grow to a preset size, and then stopping spraying the distilled water and drying properly; and (e) Screening and selecting the pellets with a size of 30-70 meshes, preferably with a size of 30-60 meshes; and (f) Putting the pellets in a boiling bed, spraying a coating liquid for sustained release on surfaces of the pellets to form a coating until a weight gain of the coating reaches 5% of total weight of the pellets so that a coated pellet form is obtained.

According to another preferred embodiment of the present invention, the medication in liquid form is prepared by the steps of: Mixing 5-10 grams of ginsenoside, 7-15 grams of *Astragalus* polysaccharide, 10-20 grams of zedoary (*Curcuma zedoaria*), 10-15 grams of river bulrush (*Sparganium stolonferum Buch.-Ham*), 10-15 grams of extract of *Ternstroemia gymnanthera*, 12-20 grams of *Fructus Ligustri Lucidi*, 5-9 grams of *licorice*, 12-19 grams of Chinese skullcap extract (*Scutellaria baicalnsis Georgi*), 15-20 grams of *Sculellaria barbata*, 13 grams of paclitaxel, 15-20 grams of micropowder of *Silybum marianum* (L.) *Gaertn.*, 50% of Cannabidiol (CBD) aqueous solution, 16% of glucose, and 5 grams of isomalto-oligosaccharides to form a mixture; Adding distilled water with five times of volume of the mixture and carrying out extraction at 80° C. for one hour and filtering, then concentrating the filtrate at 80° C. under reduced pressure to form a mixture concentrate; and Mixing, filtering, and sterilizing the mixture concentrate to obtain an oral liquid.

According to another preferred embodiment of the present invention, the medication in capsule form is prepared by the steps of: Mixing and dissolving 5-10 grams of ginsenoside, 7-15 grams of *Astragalus* polysaccharide, 10-20 grams of zedoary (*Curcuma zedoaria*), 10-15 grams of river bulrush (*Sparganium stoloniferum Buch.-Ham*), 10-15 grams of extract of *Ternstroemia gymnanthera*, 12-20 grams of *Fructus Ligustri Lucidi*, 5-9 grams of *licorice*, 12-19 grams of Chinese skullcap extract (*Scutellaria baicalnsis Georgi*), 15-20 grams of *Sculellaria barbata*, 13 grams of paclitaxel, 15-20 grams of micropowder of *Silybum marianum* (L.) *Gaertn.* 25-50% of CBD powder, and povidone K15 in absolute ethanol until completely dissolved to form a mixture; Adding inactive auxiliary materials to the mixture to prepare a pellet form; Coating the pellet form with a coating liquid for sustained release to form a coated pellet form; and Filling the coated pellet form into capsule form.

BRIEF DESCRIPTION OF THE DRAWINGS

FIG. 1 is a Table showing the Chinese name and content of the active ingredients of traditional Chinese medicine with sustained release for cancer treatment.

DETAILED DESCRIPTION OF THE PREFERRED EMBODIMENT

The present invention provides a traditional Chinese medicine for cancer treatment and a preparation method thereof. The present invention is based on the theory and principles of Traditional Chinese Medicine. In particular, the present invention provides a sustained-release preparation for treating cancer and a preparation method thereof, wherein the composition for cancer treatment is in oral form and is manufactured into a coated pellet, a capsule, or an oral liquid.

According to the present invention, the Chinese medicine is prepared by using active ingredients of: ginsenoside, Astragalus polysaccharide, zedoary (Curcuma zedoaria), river bulrush (Sparganium stoloniferum Buch.-Ham), Ternstroemia gymnanthera, Fructus Ligustri Lucidi, licorice, Chinese skullcap (Scutellaria baicalnsis Georgi), Sculellaria barbata, paclitaxel, Silybum marianum (L.) Gaertn., and Cannabidiol (CBD).

The active ingredients are Traditional Chinese medicine which is known by practitioners of Traditional Chinese medicine. The specific name of each active ingredient refers to the common and standard form used in Traditional Chinese medicine. These active ingredients can provide a body balancing and treatment effect to cancer's patients.

Pharmacological Actions:

Ginsenoside: It has the effects of nourishing vitality, strengthening the spleen and lungs, replenishing thirst, quenching thirst, anti-cancer and swelling.

Astragalus polysaccharide: It is an active ingredient extracted from Astragalus membranaceus. It is an immune booster or immune modulator. It also has antioxidant, anti-aging, disease and cancer prevention function.

Zedoary (Curcuma zedoaria) and river bulrush (Sparganium stolonferum Buch.-Ham): The combination of two can relieve collaterals, promote blood circulation, digestion and stomach, improve diet, promote the flow of qi and relieve pain, and has therapeutic effect on liver, stomach and breast cancer.

Ternstroemia gymnanthera, Fructus Ligustri Lucidi, licorice, and CBD: The combination of four has the effect of clearing heat dampness and phlegm, relieving liver and regulating qi, replenishing and relieving evil, nourishing liver and kidney, strengthening physique, and detoxifying and antibacterial. This combination is especially suitable for late-stage cancer patient. It also repairs the immune system and nervous tissue, and can effectively inhibit the generation and recurrence of cancer cells.

Chinese skullcap (Scutellaria baicalnsis Georgi): It has the effect of clearing heat and detoxifying, purging fire and drying dampness, and has therapeutic effects on liver cancer, gastric cancer, and breast cancer.

Sculellaria barbata: It has the effect of detoxifying and antibacterial, promoting blood circulation and removing stasis, reducing swelling and pain. It is commonly used in edema, malignant sores and liver cancer, and ascites due to cirrhosis.

Silybum marianum (L.) Gaertn: It has the effect of promoting liver cells, detoxification, removing heat, and replenishing and nourishing blood.

Embodiment 1

The medication of traditional Chinese medicine with sustained release for cancer treatment according to the present invention is prepared into an oral form with the following active ingredients:

5-10 grams of ginsenoside, 7-15 grams of Astragalus polysaccharide, 10-20 grams of zedoary (Curcuma zedoaria), 10-15 grams of river bulrush (Sparganium stolonferum Buch.-Ham), 10-15 grams of extract of Ternstroemia gymnanthera, 12-20 grams of Fructus Ligustri Lucidi, 5-9 grams of licorice, 12-19 grams of Chinese skullcap extract (Scutellaria baicalnsis Georgi), 15-20 grams of Sculellaria barbata, 13 grams of paclitaxel, 15-20 grams of micropowder of Silybum marianum (L.) Gaertn., and 25-50% (by percentage weight of total active ingredients) of Cannabidiol (CBD) powder or solution.

The medication of traditional Chinese medicine with sustained release for cancer treatment according to the present invention is safe to take, has low level of stimulation to gastrointestinal tract, and provides a stable drug concentration in the blood and can last for 24 hours. The medication of traditional Chinese medicine with sustained release for cancer treatment according to the present invention is particularly useful for patients suffering from toxic side effect due to conventional cancer treatment and can reduce the toxicity of conventional cancer treatment. The medication can solve the problems of hair loss, vomiting and unbearable soreness due to the cancer or the side effects of the conventional cancer treatment.

According to this embodiment, the coating raw materials are, by percentage weight:

23% Hydroxypropyl methylcellulose, 25% Magnesium stearate, appropriate amount of absolute ethanol, 30% microcrystalline cellulose, 1 g Polyethylene glycol 6000, 120 ml distilled water, and 16% of glucose.

Preparation Method 1:

Provide active ingredients: 5-10 grams of ginsenoside, 7-15 grams of Astragalus polysaccharide, 10-20 grams of zedoary (Curcuma zedoaria), 10-15 grams of river bulrush (Sparganium stolonferum Buch.-Ham), 10-15 grams of extract of Ternstroemia gymnanthera, 12-20 grams of Fructus Ligustri Lucidi, 5-9 grams of licorice, 12-19 grams of Chinese skullcap extract (Scutellaria baicalnsis Georgi), 15-20 grams of Sculellaria barbata, 13 grams of paclitaxel, 15-20 grams of micropowder of Silybum marianum (L.) Gaertn., and 25-50% (by percentage weight of total active ingredients) of Cannabidiol (CBD) powder or solution.

Wash zedoary (Curcuma zedoaria), river bulrush, Fructus Ligustri Lucidi, licorice, and Sculellaria barbata, add water and ethanol in equal part to eight times and then carry out extraction for two times. For the first time, extract the washed ingredients for three hours, filter, concentrate and dry. Then set aside. For the second time, obtain the filter residue, add water to five times and then extract the filter residue for 1.5 hours, then filter, concentrate and dry. Then, set aside.

Mix ginsenoside, Astragalus polysaccharide, extract of Ternstroemia gymnanthera, Chinese skullcap extract, micropowder of Silybum marianum (L.) Gaertn., paclitaxel, CBD powder and 60 grams of starch by a mixer.

Place all the above prepared active ingredients and microcrystalline cellulose in a fluidized bed, and according to the standard operating parameters, spray an appropriate amount of distilled water so that all the ingredients are bonded to form pellets, which are drug-loaded pellets. After the pellets grow to a certain size, stop spraying the distilled water and dry properly. Screening and selecting pellets with a size of 30-70 meshes, and preferably with a size of 30-60 meshes.

Put the drug-loaded pellets in a boiling bed. According to the standard operating parameters, surface sealing a sustained release coating liquid on the surface of the drug-loaded pellets. After the weight gain of the coating reaches 5% of total weight, stop spraying. Continue drying at 55-60° C. for 0.5 hour to obtain a pellet with sustained-release coating, which is a coated pellet.

Preparation Method 2:

In addition, the preparation method of sustained-release capsule is as follows:

Providing active ingredients consisting of: 5-10 grams of ginsenoside, 7-15 grams of *Astragalus* polysaccharide, 10-20 grams of zedoary (*Curcuma zedoaria*), 10-15 grams of river bulrush (*Sparganium stolonferum Buch.-Ham*), 10-15 grams of extract of *Ternstroemia gymnanthera*, 12-20 grams of *Fructus Ligustri Lucidi*, 5-9 grams of *licorice*, 12-19 grams of Chinese skullcap extract (*Scutellaria baicalnsis Georgi*), 15-20 grams of *Sculellaria barbata*, 13 grams of paclitaxel, 15-20 grams of micropowder of *Silybum marianum* (L.) *Gaertn.*, 25-50% (by percentage weight of total active ingredients) of CBD powder;

Mixing and dissolving the active ingredients and povidone K15 in absolute ethanol;

Adding inactive auxiliary materials after all the active ingredients and povidone K15 are completely dissolved to prepare a pellet form of anticancer composition;

Coating the pellet form with a coating liquid to form the medication in coated pellet form; and Filling the medication in coated pellet form into capsule.

Preferably, the capsule contains 0.5 g of active ingredients.

Preparation Method 3:

Providing active ingredients of: 5-10 grams of ginsenoside, 7-15 grams of *Astragalus* polysaccharide, 10-20 grams of zedoary (*Curcuma zedoaria*), 10-15 grams of river bulrush (*Sparganium stolonferum Buch.-Ham*), 10-15 grams of extract of *Ternstroemia gymnanthera*, 12-20 grams of *Fructus Ligustri Lucidi*, 5-9 grams of *licorice*, 12-19 grams of Chinese skullcap extract (*Scutellaria baicalnsis Georgi*), 15-20 grams of *Sculellaria barbata*, 13 grams of paclitaxel, 15-20 grams of micropowder of *Silybum marianum* (L.) *Gaertn.*, 50% of Cannabidiol (CBD) aqueous solution by percentage weight of total active ingredients:

Mixing the active ingredients with 16% of glucose, and 5 grams of isomalto-oligosaccharides to form a mixture, Adding distilled water with five times of volume of the mixture and carrying out extraction at 80° C. for one hour and filtering, then concentrate the filtrate at 80° C. under reduced pressure to form a mixture concentrate, Mixing, filtering, sterilizing, and filling the mixture concentrate to obtain an oral liquid.

Characteristics: The preparation method has the advantages of unique preparation process. The medication has no significant side effect, small adverse action to the body, less stimulation to the gastrointestinal tract, stable concentration in the blood inside the body, less administration frequency, and the treatment effect for each dosage can last for 24 hours. The bioavailability is remarkably improved, which enables the medication to slowly release into the body for continuous absorption. The medication is especially target for patients suffered from toxic side effects of radiotherapy and chemotherapy, which can increase the efficiency and reduce the toxicity of treatment, eliminate vomiting, hair loss, and unbearable soreness of the body.

The medication of the present invention can work with western medical treatment to increase the cure rate of patient with radiotherapy and chemotherapy treatment, and can promote blood circulation, clear away heat and assist detoxification, reduce swelling and pain, stop nausea and vomiting, improve disease resistance and prolong life.

The dosage form used in the present invention is in the oral form, which includes oral liquid form, pellet form and capsule form.

Testing and Clinical Trial

Efficacy test: mice, acute tumor cell stimulation test

Test composition: Composition of Embodiment 1 in pellet form (0.5 g active ingredient), which is prepared into an injection liquid.

Experimental animals: mice, weighing 150-250 grams, healthy and non-cancerous. 24 hours before the test, both sides of the spine were shaved (3 cm×3 cm) for skin preparation.

Test method: Inject test composition (undiluted) directly into the test object at one side of skin preparation, cover with a layer of oil yarn and fix it with adhesive tape. On the other side of skin preparation, distilled water is used as a control. Wash with warm water after four hours. Observe at 1 hour, 24 hours, 48 hours and 72 hours. According to the 'Cancer Cell Stimulation Response Score' in the 'Drug Safety Evaluation Procedures and Methods', record the cancer cell stimulation response.

Test results: According to the 'Cancer Cell Stimulation Intensity Evaluation' in the 'Drug Safety Evaluation Procedures and Methods', no normal local cell stimulation response is observed at each observation time, and the normal cell stimulation response is zero.

Clinical Test:

In the observation experiment of 195 tumor patients using the principle of random grouping, the medication of embodiment 1 is used in 127 cases. The complete cure rate is 66.57%, the total cure rate is 87.63%. In the control group, the complete cure rate is 12.86% and the total cure rate is 37.53%. There is a significant difference between the two groups (p0<01), suggesting that the medication of embodiment 1 has a good healing and treatment effect on tumor cells.

Summary of Clinical Data:

1. 127 cases in experiment group. 85 male and 42 female.

2. 68 cases in male and female control groups, 56 male and 12 female.

3. There is no significant difference between the male and female groups. (p<0.05)

Tumor classification: Classification is based on the method according to "Differential Diagnosis of Oncology Symptoms" published by Hong Kong Science and Technology Press, 1998. There is no significant difference between the two groups. (p<0.05) and the two groups are comparable.

Stage classification: Occupational lesions and tumors are classified according to clinical diagnosis, and then classified according to tumor site and nature. If the abnormal cancer cells are just observed, it is classified as early stage. If the cancer cells continue to grow, it is classified as metaphase. If the cancer cells mature and pain is appeared and metastasizes, it is advanced stage.

In periodic comparison, there is no significant difference between the two groups (p<0.05) and the two groups are comparable.

Experiment group: Take the medication of Embodiment 1 for 30 days, once a day, and 2 capsules each time. (each capsule=0.5 g)

Control group: radiotherapy and chemotherapy, and gossypol acetate, 3 times a day, 10 g each time.

Efficacy determination: According to the diagnosis of cancer, it is divided into early, middle and late stage. The efficacy comment is divided into complete cure, basic cure, improvement and ineffective. The definition of complete cure, basic cure, improvement and ineffective are as follows:

Complete cure: After half year, or more than one year, medical examination indicates no abnormality, and patient feels he/she has good health.

Basic cure: After half year, or more than one year, medical examination indicates no abnormality, but patient still feels discomfort and pain.

Improvement: After half year, or more than one year, medical examination indicates that the tumor is smaller, and the patient is recovering slowly.

Ineffective: After half year, or more than one year, medical examination indicates that the tumor is bigger gradually, and the patient feels the pain is more severe.

Efficacy Judgment of Experimental Group and Control Group:

Comparison between the two groups: The comparison of the efficacy between the two groups show that the complete cure rate and the total cure rate of the experiment group are higher than that of the control group. CT examination of the two groups show that there are significant differences between the two groups ($p<0.01$).

Discussion: After observation of 195 tumor patients (127 cases in the experimental group, 68 cases in the control group), and the two groups are grouped by disease. There is no significant difference from age, gender and severity ($p<0.05$). This shows that the two groups are similar and comparable.

The observation results show that the complete cure rate of the experimental group is 66.75%, the total cure rate is 87.63%, the complete cure rate of the control group is 12.86%, and the total cure rate is 37.53%. Comparison of the efficacy between the two groups show that the experimental group has higher efficacy effect on the early, middle and late stages than the control group. This shows that the treatment by embodiment 1 in the experiment group is significantly better than the conventional treatment in control group.

The anti-cancer medication of traditional Chinese medicine of the present invention is safe and effective for cancer treatment. The anti-cancer medication of traditional Chinese medicine of the present invention is used by more than 5000 tumors patients and some exemplary cases are described as follows:

Case 1: Female, age 48, pain in the right flank, yellow gall, fever, nausea and general weakness, weight loss. Medical examination shows that alpha-fetoglobin is positive. The left lobe of the liver has a tumor with a size of 4.7×4.5 cm and a large amount of ascites. After she has taken the composition of embodiment 1 of the present invention for about two months, her condition has improved significantly. The tumor is reduced from 4.7×4.5 cm to 2.32×2.25 cm, and the discomfort symptoms are disappeared. The patient still insisted on taking the composition of the present invention and her health condition is good during follow-up (no discomfort feelings) and can live with the tumor without discomfort symptom.

Case 2: Male, age 63, he felt epigastric pain and discomfort, which became worse day by day. After medical examination, a liver tumor of 4.3×3.7 cm is found. He has no other symptoms except for abdominal pain. The hospital diagnose as early and mid-term liver cancer, and decide to undergo surgical resection. Because the patient is unwilling to undergo surgery, he goes for traditional Chinese medicine. After he has taken the composition of embodiment 1 of the present invention for about one course of treatment, his condition has improved significantly and his abdominal pain is disappeared. In the subsequent medical examination, the result shows that the tumor has disappeared.

Case 3: Female, age 55, she feels left breast tenderness with lump. After medical examination, a tumor of 5.6×4.9 cm is found and an early to mid-term breast cancer is confirmed. She has resection and then chemotherapy for 3 times. After about 7 months, she has severe abdominal pain and a tumor at her stomach wall of 3.8×3.0 cm is found. However, she is unwilling to undergo resection again and she goes for traditional Chinese medicine. After she has taken the composition of embodiment 1 of the present invention for about one course of treatment, her condition has improved and she feels that her abdominal pain is less severe and the tumor location is soften significantly. After three courses of treatment, the patient said her pain is disappeared and she can take care of herself. After initial treatment, she thinks she is normal. At subsequent medical examination, it shows that the tumor is reduced to a size of 0.5×0.3 cm. She feels good and has no other symptoms of discomfort. She then feels like she is normal and there is no recurrence.

The medication of the present invention is suitable for use by those who are unsuitable for radiotherapy, those who are in mid- or advanced-stage and cannot undergo surgery, those who have spread and metastasized cancer, and those who cannot persist in chemoradiotherapy. The medication of the present invention can provide can treatment effect and, when used together with radiotherapy and chemotherapy treatment improve cancer treatment effect.

Evaluation and Observation of the Medication:

1. Improve body metabolism and protect the health of heart, liver, spleen and kidney.

2. It can induce cancer cell cycle arrest, inhibit tumor cell division and proliferation, promote its differentiation, prevent tumor cell growth, and make the tumor shrink or disappear.

3. Selectively inhibit Na, K, ATPase activities, stimulate reticular endothelial system proliferation and enhance the activity of phagocytic cancer cells, improve the immune system, and induce cancer cell apoptosis.

4. Protect the bone marrow hematopoietic system, stabilize the white blood cell lipid number, reduce the damage of hematopoietic cells by chemoradiotherapy and cancerous toxins.

5. It is mainly used for the treatment of liver, stomach and breast malignancies, and all have achieved different degrees of efficacy.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A medication of traditional Chinese medicine for cancer treatment, comprising: 5-10 grams of ginsenoside, 7-15 grams of *Astragalus* polysaccharide, 10-20 grams of zedoary, 10-15 grams of river bulrush, 10-15 grams of extract of *Ternstroemia gymnanthera,* 12-20 grams of *Fructus Ligustri Lucidi,* 5-9 grams of *licorice,* 12-19 grams of Chinese skullcap extract, 15-20 grams of *Sculellaria barbata,* 13 grams of paclitaxel, 15-20 grams of micropowder of *Silybum marianum* (L.) *Gaertn.*, and 25-50% by percentage weight of Cannabidiol powder, wherein said medication is in an oral form and is in the form of a coated pellet.

2. The medication of traditional Chinese medicine for cancer treatment according to claim 1, wherein said medication is prepared by the steps of:
   (a) Carrying out extraction for zedoary, river bulrush, *Fructus Ligustri Lucidi, licorice,* and *Sculellaria barbata,* to obtain a first composition;
   (b) Mixing ginsenoside, *Astragalus* polysaccharide, *Ternstroemia gymnanthera* extract, Chinese skullcap extract, *Silybum marianum* (L.) *Gaertn.* micropowder, paclitaxel, cannabidiol powder and starch by a mixer to obtain a second composition;
   (c) Placing the first composition, the second composition, and microcrystalline cellulose in a fluidized bed, and spraying distilled water so that the first composition, the second composition, and the microcrystalline cellulose are bonded to form pellets;
   (d) Allowing the pellets to grow to a preset size, and then stopping spraying the distilled water and drying properly; and
   (e) Screening and selecting the pellets with a size of 30-70 meshes; and
   (f) Putting the pellets in a boiling bed, spraying a coating liquid for sustained release on surfaces of the pellets to form a coating until a weight gain of the coating reaches 5% of total weight of the pellets so that a coated pellet form is obtained.

3. The medication of traditional Chinese medicine for cancer treatment according to claim 2, wherein the step (e) is replaced by the step of:
   (e') Screening and selecting the pellets with a size of 30-60 meshes.

4. A medication of traditional Chinese medicine for cancer treatment, comprising: 5-10 grams of ginsenoside, 7-15 grams of *Astragalus* polysaccharide, 10-20 grams of zedoary, 10-15 grams of river bulrush, 10-15 grams of extract of *Ternstroemia gymnanthera,* 12-20 grams of *Fructus Ligustri Lucidi,* 5-9 grams of *licorice,* 12-19 grams of Chinese skullcap extract, 15-20 grams of *Sculellaria barbata,* 13 grams of paclitaxel, 15-20 grams of micropowder of *Silybum marianum* (L.) *Gaertn.*, and 25-50% by percentage weight of Cannabidiol powder, wherein said medication is in an oral form and is in the form of a capsule.

5. The medication of traditional Chinese medicine for cancer treatment according to claim 4, wherein said medication is prepared by the steps of:
   (a) Mixing and dissolving 5-10 grams of ginsenoside, 7-15 grams of *Astragalus* polysaccharide, 10-20 grams of zedoary, 10-15 grams of river bulrush, 10-15 grams of extract of *Ternstroemia gymnanthera,* 12-20 grams of *Fructus Ligustri Lucidi,* 5-9 grams of *licorice,* 12-19 grams of Chinese skullcap extract, 15-20 grams of *Sculellaria barbata,* 13 grams of paclitaxel, 15-20 grams of micropowder of *Silybum marianum* (L.) *Gaertn.*, 25-50% of cannabidiol powder by percentage weight, and povidone K15 in absolute ethanol until completely dissolved to form a mixture;
   (b) Adding inactive auxiliary materials to the mixture to prepare a pellet form;
   (c) Coating the pellet form with a coating liquid for sustained release to form a coated pellet form; and
   (d) Filling the coated pellet form into capsule form.

\* \* \* \* \*